(12) United States Patent
Morimoto et al.

(10) Patent No.: US 11,013,482 B2
(45) Date of Patent: May 25, 2021

(54) PHASE CONTRAST X-RAY IMAGING SYSTEM

(71) Applicant: Shimadzu Corporation, Kyoto (JP)

(72) Inventors: Naoki Morimoto, Kyoto (JP); Kenji Kimura, Kyoto (JP); Taro Shirai, Kyoto (JP); Takahiro Doki, Kyoto (JP); Satoshi Sano, Kyoto (JP); Akira Horiba, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/636,492

(22) PCT Filed: Sep. 19, 2018

(86) PCT No.: PCT/JP2018/034674
§ 371 (c)(1),
(2) Date: Feb. 4, 2020

(87) PCT Pub. No.: WO2019/087605
PCT Pub. Date: May 9, 2019

(65) Prior Publication Data
US 2020/0249178 A1  Aug. 6, 2020

(30) Foreign Application Priority Data
Oct. 31, 2017  (JP) .............................. JP2017-211085

(51) Int. Cl.
*A61B 6/00* (2006.01)
*G01N 23/04* (2018.01)
*G01N 23/041* (2018.01)

(52) U.S. Cl.
CPC .......... *A61B 6/5205* (2013.01); *A61B 6/4035* (2013.01); *A61B 6/4291* (2013.01);
(Continued)

(58) Field of Classification Search
CPC ...... G01N 23/041; G01N 23/20; A61B 6/484; A61B 6/00; G06T 7/00; G06T 7/11
(Continued)

(56) References Cited

U.S. PATENT DOCUMENTS 7,180,979 B2 *  2/2007  Momose .............. A61B 6/4291
378/62
8,824,629 B2 *  9/2014  Ishii ..................... A61B 6/4291
378/62
(Continued)

FOREIGN PATENT DOCUMENTS

WO  2014/030115 A1  2/2014

OTHER PUBLICATIONS

International Search Report dated Nov. 20, 2018 and Written Opinion in corresponding International application No. PCT/JP2018/034674; 7 pages including Machine-generated English-language translation.

*Primary Examiner* — Thomas R Artman
(74) *Attorney, Agent, or Firm* — Maier & Maier, PLLC

(57) ABSTRACT

A phase contrast X-ray imaging system includes an X-ray source; a plurality of gratings; a detector; a grating movement mechanism; and an image processor that generates a phase contrast image. The image processor generates the phase contrast image by using a pitch of an intensity change and a function which has the pitch as a variable and expresses the intensity change in a pixel value as a grating moves.

11 Claims, 7 Drawing Sheets

FIRST EMBODIMENT (A) SHIFT IN PITCH OF INTENSITY CHANGE (B) PHASE CONTRAST IMAGE

(52) U.S. Cl.
CPC ............ *A61B 6/484* (2013.01); *A61B 6/5258* (2013.01); *G01N 23/041* (2018.02); *G21K 2207/005* (2013.01)

(58) Field of Classification Search
USPC .......................................................... 378/62
See application file for complete search history.

(56) References Cited

U.S. PATENT DOCUMENTS

| | | | | |
|---|---|---|---|---|
| 10,028,716 | B2* | 7/2018 | Rossl | A61B 6/4291 |
| 2005/0286680 | A1* | 12/2005 | Momose | A61B 6/483 |
| | | | | 378/62 |
| 2010/0246764 | A1* | 9/2010 | Itoh | G21K 7/00 |
| | | | | 378/62 |
| 2011/0235779 | A1* | 9/2011 | Ishii | A61B 6/484 |
| | | | | 378/62 |
| 2011/0243302 | A1* | 10/2011 | Murakoshi | G01N 23/041 |
| | | | | 378/62 |
| 2013/0142308 | A1* | 6/2013 | Ishii | A61B 6/484 |
| | | | | 378/62 |
| 2013/0170618 | A1* | 7/2013 | Koehler | A61B 6/4035 |
| | | | | 378/62 |
| 2014/0169524 | A1* | 6/2014 | Sperl | G01N 23/046 |
| | | | | 378/62 |
| 2014/0294148 | A1* | 10/2014 | Bernhardt | A61B 6/504 |
| | | | | 378/62 |
| 2016/0338659 | A1* | 11/2016 | Hoshino | A61B 6/032 |
| 2016/0356730 | A1* | 12/2016 | Handa | G21K 1/067 |
| 2017/0156686 | A1* | 6/2017 | Koehler | A61B 6/4035 |
| 2017/0202528 | A1* | 7/2017 | Roessl | A61B 6/06 |
| 2017/0219503 | A1* | 8/2017 | Vedantham | A61B 6/4452 |
| 2017/0343486 | A1* | 11/2017 | Tanabe | A61B 6/4476 |
| 2017/0343494 | A1* | 11/2017 | Hoshino | A61B 6/542 |
| 2018/0294065 | A1* | 10/2018 | Martens | G21K 1/04 |
| 2018/0344268 | A1* | 12/2018 | Koehler | A61B 6/542 |
| 2018/0356355 | A1* | 12/2018 | Momose | A61B 6/4291 |
| 2019/0086341 | A1* | 3/2019 | Momose | G01N 23/20 |
| 2019/0293577 | A1* | 9/2019 | Horiba | G01N 23/20 |
| 2019/0343472 | A1* | 11/2019 | Sano | A61B 6/00 |
| 2020/0158662 | A1* | 5/2020 | Horiba | A61B 6/4291 |
| 2020/0249178 | A1* | 8/2020 | Morimoto | A61B 6/484 |

* cited by examiner

FIG. 3
FIRST EMBODIMENT
(A) SHIFT IN PITCH OF INTENSITY CHANGE
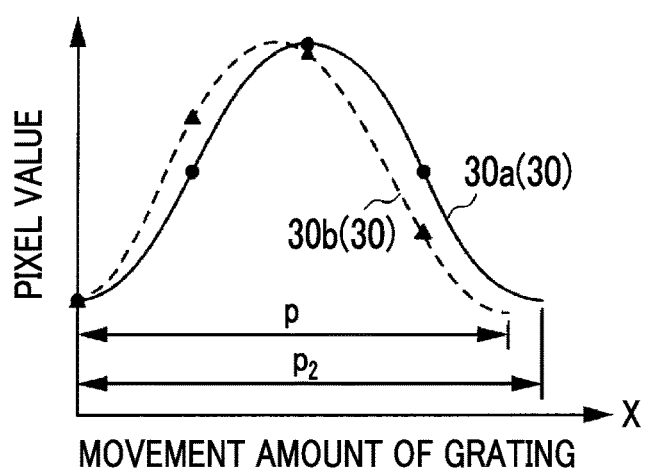
(B) PHASE CONTRAST IMAGE
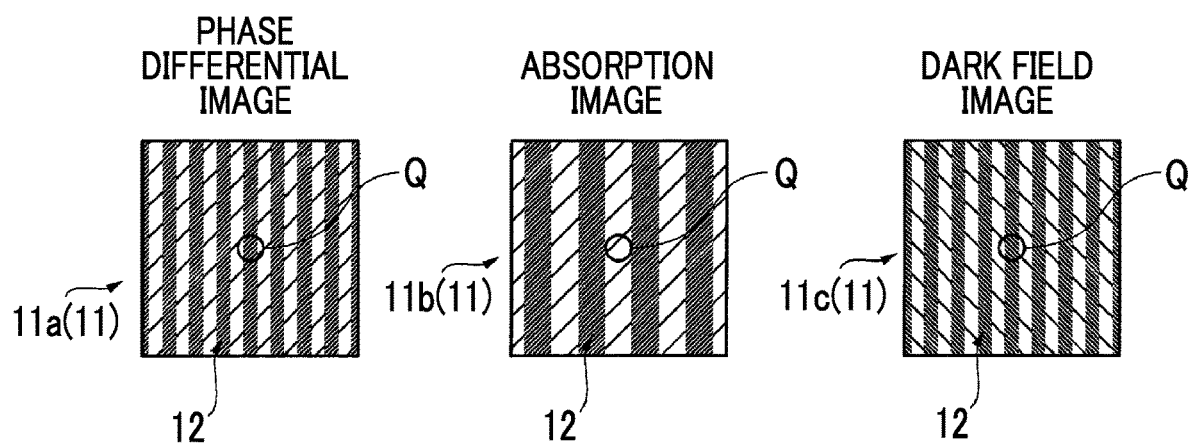

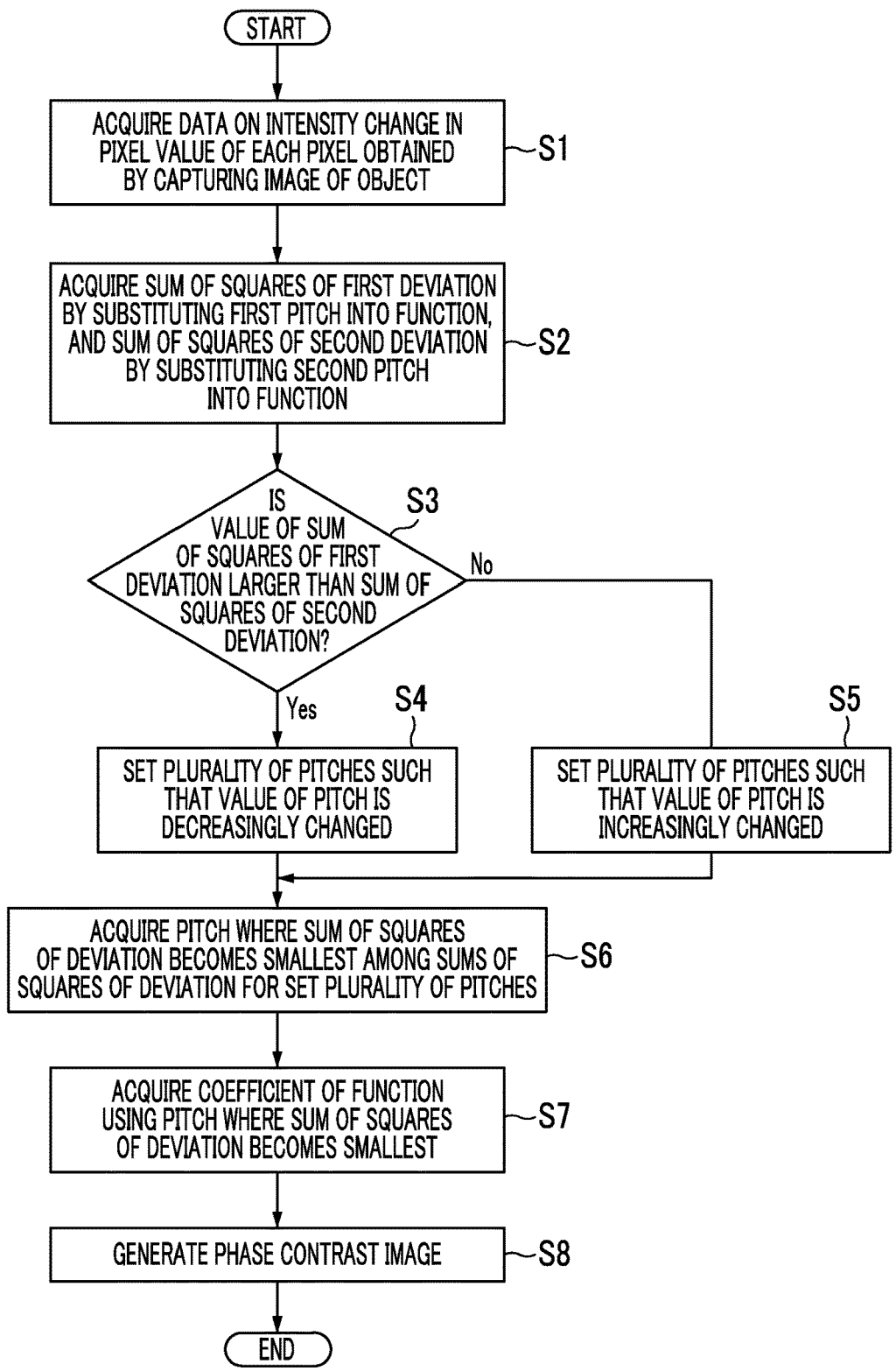

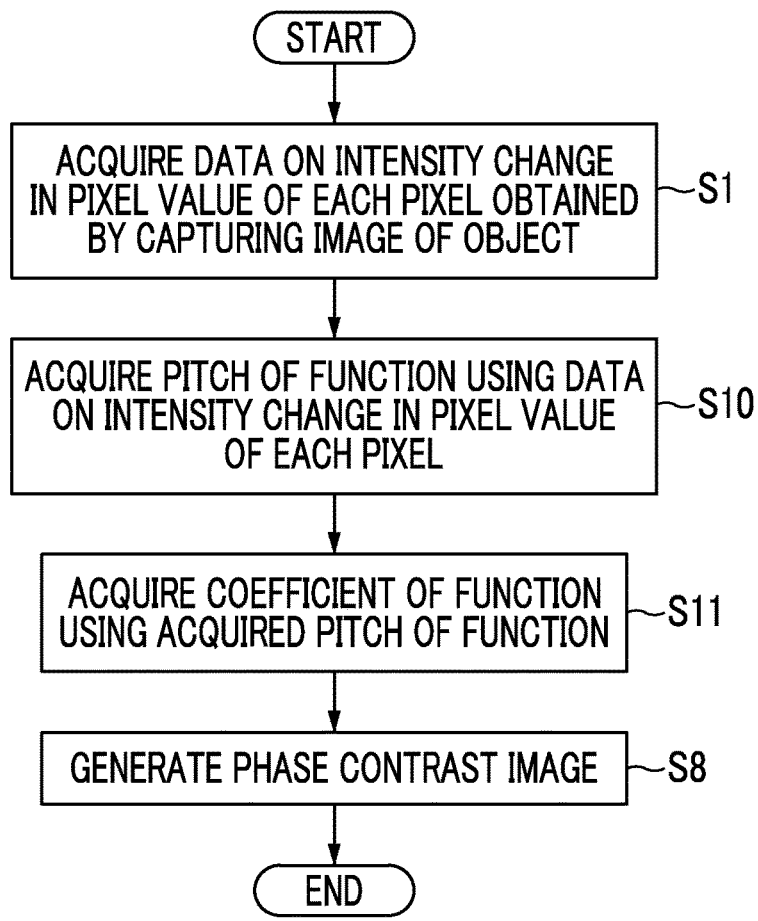

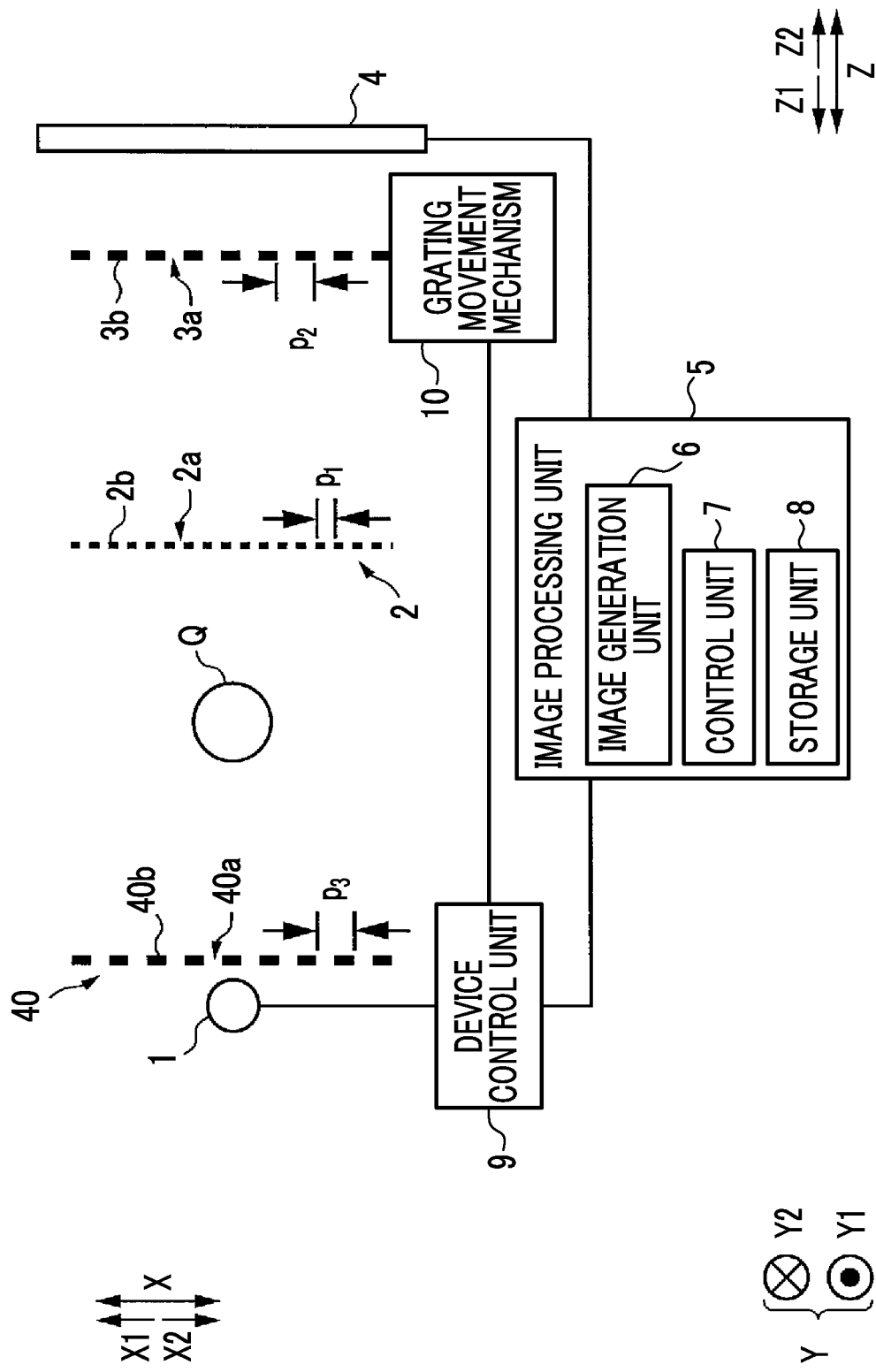

PHASE CONTRAST X-RAY IMAGING SYSTEM

FIELD

The present invention relates to a phase contrast X-ray imaging system, particularly, to a phase contrast X-ray imaging system that captures an image using a plurality of gratings.

BACKGROUND

In the related art, there is known a phase contrast X-ray imaging system that captures an image using a plurality of gratings. For example, International Publication No. 2014/030115 discloses such phase contrast X-ray imaging system.

The phase contrast X-ray imaging system disclosed in International Publication No. 2014/030115 is configured to perform X-ray imaging using a Talbot-Lau interferometer, and to generate a phase contrast image by a fringe scanning method.

Here, in the Talbot-Lau interferometer, an image is captured using a multislit, a phase grating, and an absorbent grating. Specifically, images are captured a plurality of times while translating any one of the plurality of gratings in a direction perpendicular to a grating pattern. In addition, the fringe scanning method is a technique of generating a phase contrast image based on an intensity change in the pixel value of each pixel of X-ray images which are captured a plurality of times while translationally moving a grating. Specifically, the fringe scanning method is a technique where on the assumption that the intensity change in the pixel value of each pixel of the X-ray images is data in each phase of a function of a pitch of the grating, a waveform of the function is determined, and the phase contrast image is generated based on the function where the waveform is determined. The phase contrast image includes an absorption image, a phase differential image, and a dark field image. The absorption image is an image where an object is imaged based on the attenuation of an X-ray which occurs when the X-ray passes through the object. In addition, the phase differential image is an image where the object is imaged based on a shift in the phase of the X-ray which occurs when the X-ray passes through the object. In addition, the dark field image is a visibility image which is obtained by a change in visibility based on the small-angle scattering of the object. In addition, the dark field image is also referred to as a small-angle scattering image. The "visibility" is a definition.

When the phase contrast image is generated using the fringe scanning method, images are captured while translationally moving any one of the plurality of gratings at least for one pitch of the grating in the direction perpendicular to the grating pattern. Specifically, in the fringe scanning method, images are captured while translationally moving the grating by 1/N of the pitch of the grating in the direction perpendicular to the grating pattern. Therefore, a total movement amount of the grating when the grating is translationally moved N times becomes equal to the pitch of the grating to be moved. In addition, since the total movement amount of the grating becomes equal to the pitch of the grating to be moved, the pitch of the intensity change in the pixel value of each pixel becomes equal to the pitch of the grating. Incidentally, N is a positive integer.

[PTL 1] International Publication No. 2014/030115

SUMMARY

However, in the general fringe scanning method used in the phase contrast X-ray imaging system disclosed in International Publication No. 2014/030115, since the phase contrast image is generated on the assumption that the intensity change in the pixel value of each pixel of the X-ray image is data at a phase point of a pitch 1/N, if the movement amount of the grating in each step is not equal to the pitch 1/N due to, for example, a change in the relative position of the grating by a thermal change or the accuracy of movement of a grating movement mechanism, the waveform of the function deviates from actual data. Therefore, if a shift occurs between the total movement amount of the grating and the pitch of the grating, an artifact occurs in an image to be obtained, which is a problem.

The present invention is made to solve the problem described above, and an object of the present invention is to provide a phase contrast X-ray imaging system that is capable of preventing an artifact from occurring in a phase contrast image to be obtained even though a shift occurs between a total movement amount of a grating in a direction perpendicular to a grating pattern and a pitch of the grating. Incidentally, the shift between the total movement amount of the grating in the direction perpendicular to the grating pattern and the pitch of the grating is a very small shift due to a thermal change, the accuracy of a grating movement mechanism, or the like.

According to an aspect of the present invention, in order to achieve the object, there is provided a phase contrast X-ray imaging system including an X-ray source; a plurality of gratings including a first grating that is irradiated with an X-ray from the X-ray source, and a second grating that is irradiated with the X-ray from the first grating; a detector that detects the X-ray irradiated from the X-ray source; a grating movement mechanism that moves at least one of the plurality of gratings; and an image processor that generates a phase contrast image based on an intensity change indicating a change in a pixel value of each pixel detected by the detector, in which the image processor generates the phase contrast image by using a pitch of the intensity change and a function which has the pitch as a variable and expresses the intensity change in the pixel value as the grating moves.

The phase contrast X-ray imaging system according to the aspect of the present invention includes, as described above, the image processor that generates the phase contrast image by using the pitch of the intensity change and the function which has the pitch as a variable and expresses the intensity change in the pixel value as the grating moves. Therefore, since the pitch p of the function is a variable, it is possible to approximate the pitch p of the intensity change, which is actually acquired by moving the grating, by obtaining an optimal solution for the pitch p of the function. As a result, even though a shift occurs between the pitch of the intensity change in the pixel value of each pixel and the pitch of the grating, since it is possible to adapt the pitch of the function to the pitch of the intensity change, it is possible to prevent an artifact from occurring in the phase contrast image to be obtained.

In the phase contrast X-ray imaging system according to the aspect, preferably, the pitch of the intensity change is a pitch including at least one shift of a shift in a pitch of the grating and a shift in a movement amount of the grating by the grating movement mechanism. Therefore, even though a shift occurs in either of the pitch of the grating and the movement amount of the grating (or, even though a shift occurs in both), it is possible to prevent the artifact from occurring in the phase contrast image to be generated by adapting the pitch (variable) of the function to the pitch of the intensity change which includes the shift.

In the phase contrast X-ray imaging system according to the aspect, preferably, the image processor determines the pitch of the intensity change based on data on the intensity change which is acquired by moving at least one of the plurality of gratings, and the function. According to the configuration described above, it is possible to acquire the pitch of the intensity change from the actually measured data on the intensity change. As a result, even though a shift occurs between the pitch of the intensity change and the pitch of the grating, it is possible to acquire the pitch of the intensity change which includes the shift.

In the phase contrast X-ray imaging system according to the aspect, preferably, the image processor determines the pitch of the intensity change by fitting a waveform shape of the intensity change and a waveform shape of the function to each other. According to the configuration described above, it is possible to determine the pitch of the intensity change based on the deviation between the waveform shape of the intensity change and the waveform shape of the function. As a result, since it is possible to determine the pitch of the intensity change by comparing together deviations acquired using a plurality of the pitches, for example, compared to the case where the pitch of the intensity change is determined by performing image processing on images acquired using a plurality of the pitches, it is possible to further simplify the process of determining the pitch of the intensity change.

In this case, preferably, the image processor obtains a deviation between the waveform shape of the intensity change and the waveform shape of the function using, as the pitch, at least both of a value which is larger than a design value for a pitch of the grating moved by the grating movement mechanism and a value which is smaller than the design value. According to the configuration described above, whether the pitch where the deviation becomes smallest is a value larger than the design value for the pitch of the grating or a value smaller than the design value can be determined by comparing a deviation calculated using the value larger than the design value for the pitch of the grating with a deviation calculated using the value smaller than the design value for the pitch of the grating. As a result, it is possible to easily determine the pitch where the deviation becomes smallest.

In the configuration where the pitch of the intensity change is determined by fitting the waveform shape of the intensity change and the waveform shape of the function to each other, preferably, the image processor acquires a coefficient of the function which corresponds to a predetermined pitch, and acquires a deviation between the waveform shape of the intensity change and the waveform shape of the function based on the coefficient and the predetermined pitch. According to the configuration described above, it is possible to acquire the deviation which corresponds to the predetermined pitch. As a result, it is possible to easily determine the pitch where the deviation becomes smallest by comparing together deviations which correspond to a plurality of the pitches.

In the phase contrast X-ray imaging system according to the aspect, preferably, the image processor acquires a coefficient of the function from a pitch of the intensity change which is acquired in advance, and generates the phase contrast image based on the acquired coefficient and the pitch of the intensity change which is acquired in advance. Here, since the pitch of the grating is a very small value, the pitch may be slightly shifted due to manufacturing errors. Even though the pitch which is slightly shifted from the pitch of the grating is already known, in a general fringe scanning method, it is necessary to acquire data for a pitch k/N. However, if the accuracy of the grating movement mechanism is not sufficient, since it is not possible to translationally move the grating by a movement amount obtained by dividing the already-known pitch by N, it is not possible to acquire the data for the pitch k/N, and the artifact occurs. Since it is possible to acquire a shift in the pitch of the grating in advance by measurement, it is possible to acquire a shift between the pitch of the intensity change and the pitch of the grating in advance. Therefore, according to the configuration described above, it is possible to acquire the coefficient of the function by fitting an actual measurement value and the function, into which the pitch of the intensity change which is acquired in advance is substituted, to each other. As a result, even though the movement amount of the grating is shifted, it is possible to determine the function which accurately approximates actual data, and it is possible to prevent the artifact from occurring in the phase contrast image to be generated. Incidentally, k is a positive integer from 1 to N.

In the phase contrast X-ray imaging system according to the aspect, preferably, the plurality of gratings further include a third grating that is disposed between the X-ray source and the first grating. According to the configuration described above, it is possible to enhance the coherence of an X-ray irradiated from the X-ray source due to the third grating. As a result, since it is possible to form a self-image of the first grating without depending on a focal diameter of the X-ray source, it is possible to improve the degree of freedom in selecting the X-ray source.

According to the present invention, as described above, it is possible to provide a phase contrast X-ray imaging system that is capable of preventing an artifact from occurring in a phase contrast image to be obtained even though a shift occurs between a total movement amount of a grating in a direction perpendicular to a grating pattern and a pitch of the grating.

BRIEF DESCRIPTION OF DRAWINGS

FIG. 3(A) is a graph for describing a shift in the pitch of the intensity change in the pixel value of each pixel, and FIG. 3(B) is a schematic view for describing an artifact occurring in a phase contrast image to be generated.

FIG. 5 is a flowchart for describing a method for generating a phase contrast image according to the first embodiment of the present invention.

FIG. 6 is a flowchart for describing a method for generating a phase contrast image according to a second embodiment of the present invention.

FIG. 7 is a schematic diagram of a phase contrast X-ray imaging system according to a modification example of the first embodiment of the present invention when seen from the direction Y.

DETAILED DESCRIPTION

Hereinafter, embodiments in which the present invention is materialized will be described based on the drawings.

First Embodiment

A configuration of a phase contrast X-ray imaging system 100 according to a first embodiment of the present invention will be described with reference to FIGS. 1 to 5.

(Configuration of Phase Contrast X-Ray Imaging System)

Firstly, the configuration of the phase contrast X-ray imaging system 100 according to the first embodiment of the present invention will be described with reference to FIG. 1.

Figure 1:
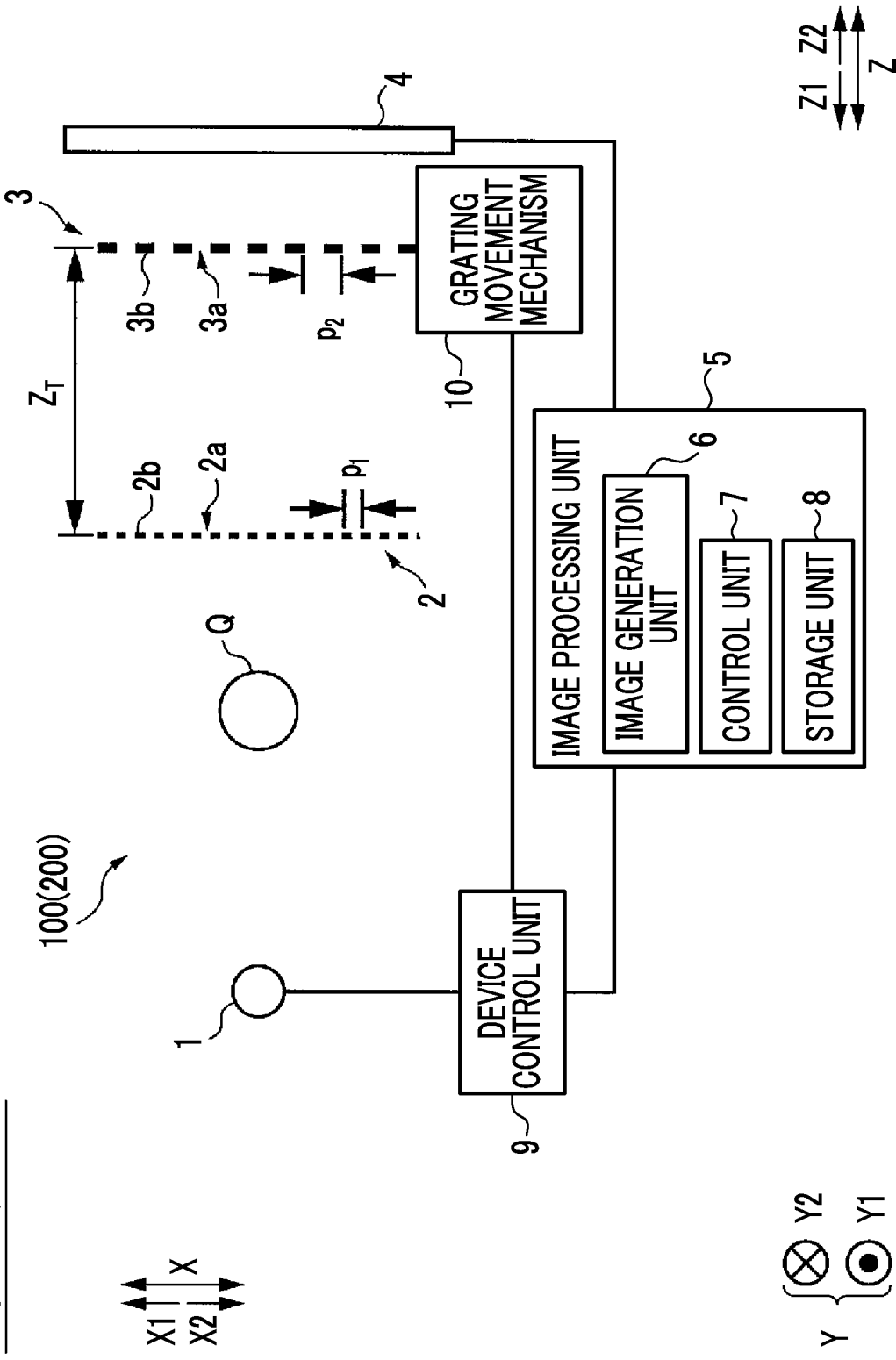
FIG. 1 is a schematic diagram of a phase contrast X-ray imaging system according to a first embodiment of the present invention when seen from a direction Y.

FIG. 1 is a diagram of the phase contrast X-ray imaging system 100 when seen from a direction Y. As illustrated in FIG. 1, the phase contrast X-ray imaging system 100 includes an X-ray source 1; a first grating 2; a second grating 3; a detector 4; an image processor 5; a device control unit 9; and a grating movement mechanism 10. Incidentally, in this specification, a direction from the X-ray source 1 toward the first grating 2 is a direction Z2, and a direction reverse thereto is a direction Z1. In addition, a rightward and leftward direction in a plane perpendicular to a direction Z is the direction Y, a direction toward the back of the drawing sheet is a direction Y2, and a direction toward the front of the drawing sheet is a direction Y1. In addition, an upward and downward direction in the plane perpendicular to the direction Z is a direction X, an upward direction is a direction X1, and a downward direction is a direction X2.

The X-ray source 1 is configured to generate an X-ray and to irradiate the detector 4 (direction Z2) with the generated X-ray if a high voltage is applied to the X-ray source 1 based on a signal from the device control unit 9.

The first grating 2 has a plurality of slits 2a and X-ray phase change portions 2b which are arranged at a predetermined pitch $p_1$ in the direction X. Each of the slit 2a and the X-ray phase change portion 2b extends straightly. In addition, the slit 2a and the X-ray phase change portion 2b extend in parallel to each other. The first grating 2 is a so-called phase grating.

The first grating 2 is disposed between the X-ray source 1 and the second grating 3, and is irradiated with an X-ray from the X-ray source 1. The first grating 2 is provided so as to form a self-image 20 (refer to FIG. 2) of the first grating 2 using the Talbot effect. If an X-ray having coherence passes through a grating provided with slits, an image (self-image 20) of the grating is formed at a position which is a predetermined distance (Talbot distance) apart from the grating. This refers to the Talbot effect.

The second grating 3 has a plurality of radioparent portions 3a and X-ray absorbent portions 3b which are arranged at a predetermined pitch $p_2$ in the direction X. Each of the radioparent portion 3a and the X-ray absorbent portion 3b extends straightly. In addition, the radioparent portion 3a and the X-ray absorbent portion 3b extend in parallel to each other. The second grating 3 is a so-called absorbent grating. The first grating 2 and the second grating 3 are gratings having different roles; however, each of the slit 2a and the radioparent portion 3a transmits an X-ray. In addition, the X-ray absorbent portion 3b plays a role in shielding an X-ray. The X-ray phase change portion 2b changes an X-ray phase due to a difference in refractive index between the slit 2a and the X-ray phase change portion 2b.

The second grating 3 is disposed between the first grating 2 and the detector 4, and is irradiated with an X-ray passing through the first grating 2. In addition, the second grating 3 is disposed at a position which is the Talbot distance apart from the first grating 2. The second grating 3 interferes with the self-image 20 of the first grating 2 to form moire fringes (not illustrated) on a front detection surface of the detector 4.

The detector 4 is configured to detect an X-ray, to transduce the detected X-ray into an electric signal, and to read the converted electric signal as an image signal. The detector 4 is, for example, a flat panel detector (FPD). The detector 4 is formed of a plurality of transduction elements (not illustrated) and pixel electrodes (not illustrated) which are disposed on the plurality of transduction elements. The plurality of transduction elements and the pixel electrodes are arranged in an array at a predetermined pitch (pixel pitch) in the direction X and the direction Y. In addition, the detector 4 is configured to output the acquired image signal to the image processor 5.

The image processor 5 includes an image generation unit 6; a control unit 7; and a storage unit 8. The image generation unit 6 is configured to generate an X-ray image (not illustrated) based on the image signal output from the detector 4. In addition, the image generation unit 6 is configured to generate a phase contrast image 11 (refer to FIG. 3(B)) based on the generated X-ray image. The image generation unit 6 includes a processor such as a graphics processing unit (GPU) or a field-programmable gate array (FPGA) configured for image processing.

In addition, the control unit 7 is configured to acquire a pitch (period) p of an intensity change 30 (refer to FIG. 2) of the X-ray detected by the detector 4, and the like. A detailed configuration where the control unit 7 acquires the pitch p of the intensity change 30 will be described later. In addition, the control unit 7 includes a processor such as a central processing unit (CPU).

The storage unit 8 is configured to store the X-ray image generated by the image generation unit 6, a program for generating the phase contrast image 11, and the like. The storage unit 8 includes a hard disk drive (HDD), a non-volatile memory, or the like.

The device control unit 9 is configured to stepwise move, via the grating movement mechanism 10, the second grating 3 in a direction (direction X) perpendicular to a direction (direction Y) of a grating pattern in a grating plane. In addition, the device control unit 9 includes a processor such as a CPU.

The grating movement mechanism 10 is configured to stepwise move the second grating 3 in the direction (direction X) perpendicular to the direction (direction Y) of the grating pattern of the grating in the grating plane (in a plane XY), based on a signal from the device control unit 9. Specifically, the grating movement mechanism 10 divides the pitch $p_2$ of the second grating 3 into N steps, and stepwise moves the second grating 3 in a step of $p_2/N$. Incidentally, N is a positive integer, and in the first embodiment, for example, N=4. In addition, the grating movement mechanism 10 includes a stepping motor, a piezo actuator, or the like.

(Configuration for Acquiring Intensity Change in Pixel Value of Each Pixel)

Subsequently, a configuration where the image processor 5 acquires the intensity change 30 in the pixel value of each pixel will be described with reference to FIG. 2.

Figure 2:
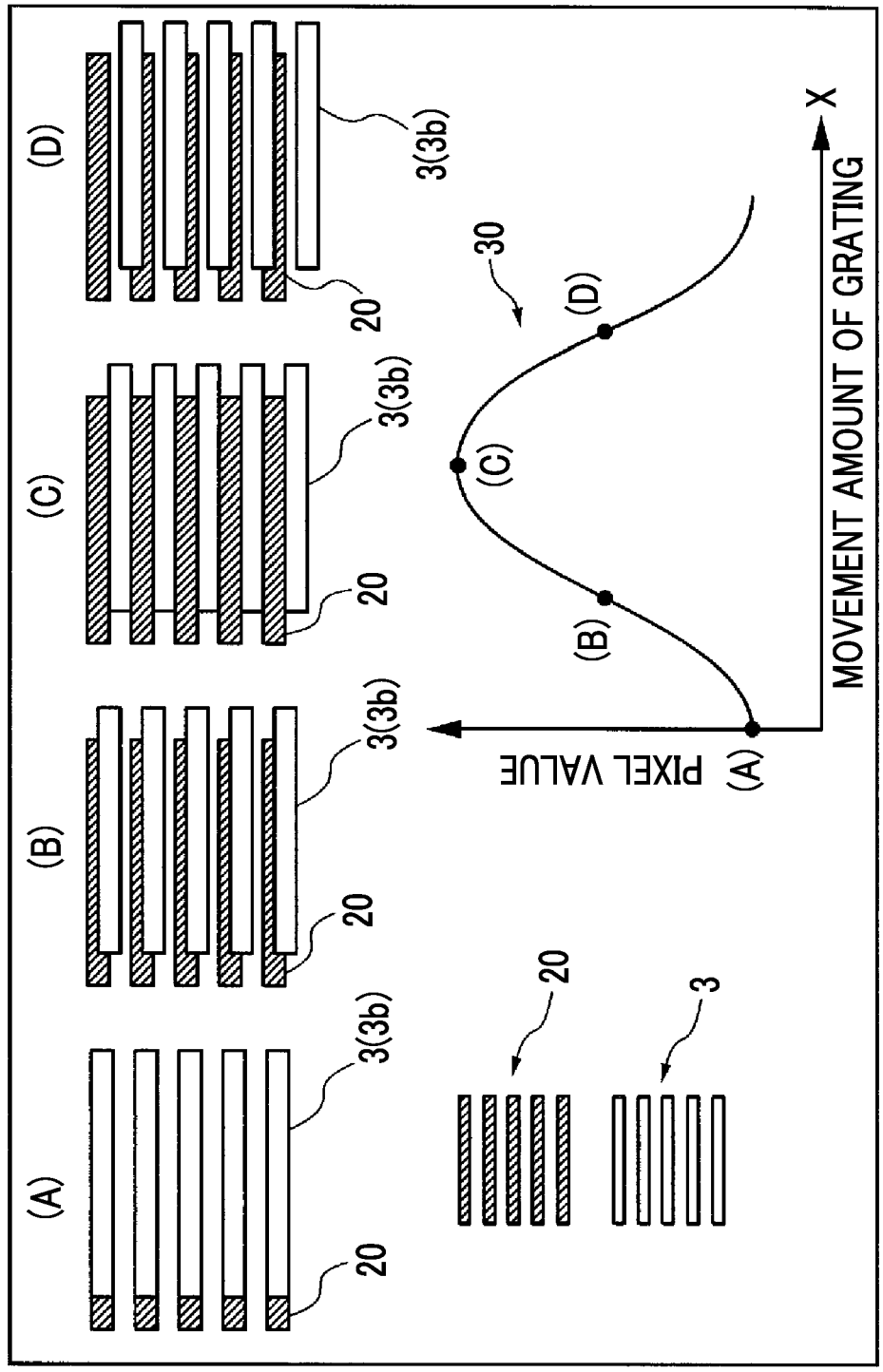
FIG. 2 is a schematic view for describing a process of acquiring an intensity change in the pixel value of a pixel.

FIGS. 2(A) to 2(D) are schematic views showing a positional relationship between the self-image 20 of the first grating 2 and the second grating 3 when the grating movement mechanism 10 translationally moves the second grating 3 and the image generation unit 6 according to the first embodiment generates the phase contrast image 11 by a fringe scanning method, and FIG. 2 is a graph showing the intensity change 30 in the pixel value of each pixel of the X-ray image captured while translationally moving the second grating 3.

In the first embodiment, the device control unit 9 is configured to capture images while translationally moving, via the grating movement mechanism 10, the second grating 3 four times in a step of $p_2/4$. Namely, in the first embodiment, as illustrated in FIGS. 2(A) to 2(D), the phase contrast X-ray imaging system 100 is configured to capture images while moving the second grating 3 in a step of $p_2/4$ in the direction X2. In addition, the control unit 7 acquires, as shown in the graph in FIG. 2, the intensity change 30 as an intensity change in the pixel value of each pixel when capturing images while moving the second grating 3 in a step of $p_2/4$ in the direction X2.

Description of Comparative Example

Here, in a general fringe scanning method, the phase contrast image 11 is generated based on the intensity change 30 in an X-ray image captured in a state where an object Q is not disposed and the intensity change 30 in an X-ray image captured in a state where the object Q is disposed. For example, a case where images are captured while the second grating 3 is translated N times can be considered.

The intensity of an X-ray detected by the detector 4 when an image is captured in a state where the object Q is disposed is $I_k(x, y)$, the intensity of an X-ray when an image is captured in a state where the object Q is not disposed is $I_{0k}(x, y)$, and $S(x, y)$ and $S_0(x, y)$ are defined as follows.

[Numeral 1]

$$S(x, y) = \sum_{k=1}^{N} I_k(x, y) \exp\left(-\frac{2i\pi k}{N}\right) \quad (1)$$

$$S_0(x, y) = \sum_{k=1}^{N} I_{0k}(x, y) \exp\left(-\frac{2i\pi k}{N}\right) \quad (2)$$

Here, k is a positive integer from 1 to N. In addition, x and y are an x coordinate and a y coordinate of each pixel.

The pixel value of each of pixels representing a phase differential image 11a can be calculated by the following equation (3) using the equations (1) and (2). Incidentally, a pixel value $\Phi(x, y)$ of each pixel of the phase differential image 11a is a difference in phase value between when the object Q is disposed and when the object Q is not disposed.

[Numeral 2]

$$\varphi_x(x, y) = \frac{p_2}{2\pi Z_T} \arg\left[\frac{S(x, y)}{S_0(x, y)}\right] \quad (3)$$

Here, $Z_T$ is a distance between the first grating 2 and the second grating 3. In addition, a pixel value $T(x, y)$ of each pixel representing an absorption image 11b is expressed in the following equation (4).

[Numeral 3]

$$T(x, y) = \frac{\sum_{k=1}^{N} I_k(x, y)}{\sum_{k=1}^{N} I_{0k}(x, y)} \quad (4)$$

$V(x, y)$ which is a visibility when the object Q is disposed and $V_0(x, y)$ which is a visibility when the object Q is not disposed are expressed in the following equations (5) and (6).

[Numeral 4]

$$V(x, y) = \frac{2|S(x, y)|}{\sum_{k=1}^{N} I_k(x, y)} \quad (5)$$

$$V_0(x, y) = \frac{2|S_0(x, y)|}{\sum_{k=1}^{N} I_{0k}(x, y)} \quad (6)$$

Since a dark field image 11c is a visibility ratio between when the object Q is disposed and the object Q is not disposed, the dark field image 11c is expressed in the following equation (7).

[Numeral 5]

$$D(x, y) = \frac{V(x, y)}{V_0(x, y)} = \frac{|S(x, y)|}{|S_0(x, y)|} \Big/ T(x, y) \quad (7)$$

As shown in the equations (1) and (2), in the general fringe scanning method, the phase contrast image 11 is imaged based on a value calculated on the assumption that the second grating 3 is moved only by a value, which is obtained by dividing the pitch $p_2$ of the second grating 3 by the number of steps, per step. In other words, since the equations (1) and (2) are on the assumption that an image to be acquired in each step is an image in each of phases 1/4, 2/4, 3/4, and 4/4 of the pitch $p_2$ of the second grating 3, it is necessary to reliably acquire an image in each of the phases 1/4 to 4/4 by capturing images while translationally moving the second grating 3. Therefore, if a shift occurs between the pitch p of the intensity change 30 to be acquired and the pitch $p_2$ of the second grating 3, since a calculation is performed using an image (pixel value) in a phase which is shifted from each of the phases 1/4 to 4/4, an artifact 12 is formed in the phase contrast image 11 to be generated.

(Shift in Pitch of Intensity Change)

Subsequently, the artifact 12 occurring in the phase contrast image 11 when a shift occurs between the pitch p of the intensity change 30 and the pitch $p_2$ of the second grating 3 will be described with reference to FIG. 3.

The graphs illustrated in FIG. 3(A) schematically show an intensity change 30a (solid line graph) when the pitch p of the intensity change 30 coincides with the pitch $p_2$ of the second grating 3, and an intensity change 30b (dotted line graph) when a shift occurs between the pitch p of the intensity change 30 and the pitch p₂ of the second grating 3. Incidentally, the intensity change 30b is actually N points data; however, in the example shown in FIG. 3(A), each of the N points data is regarded as data for a pitch k/N. Here, in the phase contrast X-ray imaging system 100, the second grating 3 may be deformed due to heat generated from the X-ray source 1. If the second grating 3 is deformed, the pitch p₂ of the second grating 3 changes. In addition, the grating movement mechanism 10 is configured to move the second grating 3 in parallel to the first grating 2; however, due to a positional shift during installation, or the like, a movement direction of the second grating 3 may not be parallel to the first grating 2. As described above, if the pitch p₂ of the second grating 3 changes and/or a shift occurs in the movement direction of the second grating 3, a shift occurs between a total movement amount of the second grating 3 in the direction (direction X) perpendicular to the direction (direction Y) of the grating pattern and the pitch p₂ of the second grating 3. If a shift occurs between the total movement amount of the second grating 3 in the direction (direction X) perpendicular to the direction (direction Y) of the grating pattern and the pitch p₂ of the second grating 3, the pitch p of the intensity change 30 acquired by the control unit 7 is shifted from the pitch p₂ of the second grating 3. Namely, the pitch p of the intensity change 30 is the pitch p including at least one shift of a shift in the pitch p₂ of the second grating 3 and a shift in the movement amount of the second grating 3 by the grating movement mechanism 10.

In the general fringe scanning method, the phase contrast image 11 is generated, as shown in the equations (1) to (7), by applying the acquired intensity change 30b to a function which expresses the intensity change 30a having the same pitch as the pitch p₂ of the second grating 3. Therefore, if in a state where a shift occurs between the pitch p of the intensity change 30 and the pitch p₂ of the second grating 3, the phase contrast image 11 is generated by the general fringe scanning method using the equations (1) to (8), as illustrated in FIG. 3(B), the artifact 12 with a fringe shape is formed in each image.

Then, in the first embodiment, the image processor 5 is configured to generate the phase contrast image 11 by using the pitch p of the intensity change 30b and a function which has the pitch as a variable and expresses the intensity change 30b in pixel value as the grating moves. Specifically, the image generation unit 6 generates the phase contrast image 11 by performing the following process such that even in a state where a shift occurs between the pitch p of the intensity change 30 and the pitch p₂ of the second grating 3, the artifact 12 can be prevented from occurring in the phase contrast image 11.

(Process of Generating Phase Contrast Image)

In the first embodiment, the control unit 7 is configured to determine the pitch p of the intensity change 30b based on data on the intensity change 30b acquired by moving the second grating 3, and the function. Specifically, the control unit 7 is configured to determine the pitch p of the intensity change 30b by fitting a waveform shape of the intensity change 30b and a waveform shape of the function to each other. The control unit 7 is configured to determine coefficients a to c of the function, and to acquire the pitch p where a sum Z of squares of deviation of the function becomes smallest by performing the least square fitting on N data points on the acquired intensity change 30b.

X coordinates $x_k$ of the N data points can be expressed in the following equation (8).

[Numeral 6]

$$x_k = p_2 \frac{k}{N} \quad (8)$$

A function expressed by the following equation (9) is used in performing fitting.

[Numeral 7]

$$y = a\sin\frac{2\pi}{p}x + b\cos\frac{2\pi}{p}x + c \quad (9)$$

Here, p is the pitch of the intensity change 30b. In addition, a, b, and c are the coefficients of the function which are determined if the pitch p is determined.

The image processor 5 is configured to acquire the coefficients a to c of the equation (9) which correspond to a predetermined pitch. In addition, the control unit 7 is configured to acquire the sum Z of squares of deviation between the waveform shape of the intensity change 30b based on the acquired coefficients a to c and the predetermined pitch p, and a waveform shape of the equation (9). Specifically, the control unit 7 is configured to acquire the pitch p of the equation (9) by calculating the sum Z of squares of deviation between the function of the equation (9) and the N data points. The sum Z of squares of deviation can be expressed as shown in the following equation (10).

[Numeral 8]

$$Z = \sum_{k=1}^{N} (a\sin mx_k + b\cos mx_k + c - y_k)^2 \quad (10)$$

Here, m is a frequency of the intensity change 30b, and m=2π/p.

In the first embodiment, the control unit 7 partially differentiates the coefficients a, b, and c of the equation (10) so as to perform fitting using the least square method. The partial differentiation of the coefficients a, b, and c is expressed in the following equations (11) to (13).

[Numeral 9]

$$\frac{\partial Z}{\partial a} = 2\sum_{k=1}^{N} [\sin mx_k (a\sin mx_k + b\cos mx_k + c - y_k)] \quad (11)$$

$$\frac{\partial Z}{\partial b} = 2\sum_{k=1}^{N} [\cos mx_k (a\sin mx_k + b\cos mx_k + c - y_k)] \quad (12)$$

$$\frac{\partial Z}{\partial c} = 2\sum_{k=1}^{N} [a\sin mx_k + b\cos mx_k + c - y_k] \quad (13)$$

Here, $y_k$ is the pixel value of each pixel.

According to the definition of the least square method, since a, b, and c which cause each of the equations (11) to (13) to become zero may be obtained, the equations (11) to (13) are transformed into the following equations (14) to (16).

[Numeral 10]

$$a\sum_{k=1}^{N}(\sin mx_k \sin mx_k) + b\sum_{k=1}^{N}(\sin mx_k \cos mx_k) + c\sum_{k=1}^{N}(\sin mx_k) = \sum_{k=1}^{N}(y_k \sin mx_k) \quad (14)$$

$$a\sum_{k=1}^{N}(\sin mx_k \cos mx_k) + b\sum_{k=1}^{N}(\cos mx_k \cos mx_k) + c\sum_{k=1}^{N}(\cos mx_k) = \sum_{k=1}^{N}(y_k \cos mx_k) \quad (15)$$

$$a\sum_{k=1}^{N}(\sin mx_k) + b\sum_{k=1}^{N}(\cos mx_k) + c\sum_{k=1}^{N}(1) = \sum_{k=1}^{N}(y_k) \quad (16)$$

The coefficients a, b, and c can be expressed in the following equations (17) to (19) by solving simultaneous equations including the equations (14) to (16).

[Numeral 11]

$$a = \frac{a_1}{d} \quad (17)$$

$$b = \frac{b_1}{d} \quad (18)$$

$$c = \frac{c_1}{d} \quad (19)$$

At the time, each of $a_1$, $b_1$, $c_1$, and d can be expressed in the following equations (20) to (23).

[Numeral 12]

$$a_1 = (\sum \sin mx)(\sum \cos mx)(\sum y\cos mx) + \quad (20)$$
$$(\sum y)(\sum \cos mx)(\sum \sin mx \cos mx) +$$
$$(\sum 1)(\sum y\sin mx)(\sum \cos mx \cos mx) -$$
$$(\sum 1)(\sum y\cos mx)(\sum \sin mx \cos mx) - (\sum \cos mx)(\sum \cos mx)$$
$$(\sum y\sin mx) - (\sum y)(\sum \sin mx)(\sum \cos mx \cos mx)$$

$$b_1 = (\sum 1)(\sum y\cos mx)(\sum \sin mx \sin mx) + \quad (21)$$
$$(\sum \sin mx)(\sum \cos mx)(\sum y\sin mx) +$$
$$(\sum y)(\sum \sin mx)(\sum \sin mx \cos mx) -$$
$$(\sum \sin mx)(\sum \sin mx)(\sum y\cos mx) -$$
$$(\sum y)(\sum \cos mx)(\sum \sin mx \sin mx) -$$
$$(\sum 1)(\sum y\sin mx)(\sum \sin mx \cos mx)$$

$$c_1 = (\sum \sin mx)(\sum \sin mx \cos mx)(\sum y\cos mx) + \quad (22)$$
$$(\sum \cos mx)(\sum \sin mx \cos mx)(\sum y\sin mx) +$$
$$(\sum y)(\sum \sin mx \sin mx)(\sum \cos mx \cos mx) -$$
$$(\sum \cos mx)(\sum \sin mx \sin mx)(\sum y\cos mx) -$$
$$(\sum y)(\sum \sin mx \cos mx)(\sum \sin mx \cos mx) - \sum \sin mx)$$
$$(\sum \cos mx \cos mx)(\sum y\sin mx)$$

$$d = (\sum \sin mx)(\sum \cos mx)(\sum \sin mx \cos mx) + \quad (23)$$
$$(\sum \sin mx)(\sum \cos mx)(\sum \sin mx \cos mx) +$$
$$(\sum 1)(\sum \sin mx \sin mx)(\sum \cos mx \cos mx) -$$
$$(\sum \sin mx)(\sum \sin mx)(\sum \cos mx \cos mx) -$$
$$(\sum \cos mx)(\sum \cos mx)(\sum \sin mx \sin mx) -$$
$$(\sum 1)(\sum \sin mx \cos mx)(\sum \sin mx \cos mx)$$

The coefficients a, b, and c acquired from the equations (17) to (19) and the pitch p (frequency m) included in the equation (9) are unknown numbers. Therefore, in the first embodiment, the image processor 5 is configured to acquire the pitch p where the sum Z of squares of deviation becomes smallest. In the example shown in FIG. 3(A), the pitch p of the intensity change 30*b* is shifted to become smaller than the pitch $p_2$ of the second grating 3. For this reason, the control unit 7 may acquire the sum Z of squares of deviation using a plurality of the pitches p, the values of which are smaller than the pitch $p_2$ of the second grating 3. However, actually, the pitch p of the intensity change 30*b* is an unknown number. For this reason, the control unit 7 is configured to obtain the sum Z of squares of deviation between the waveform shape of the intensity change 30*b* and the waveform shape of the equation (9) using, as the pitch, at least both of a value which is larger than a design value for the pitch $p_2$ of the second grating 3 moved by the grating movement mechanism 10 and a value which is smaller than the design value.

For example, the control unit 7 acquires a first deviation using the value larger than the pitch $p_2$ of the second grating 3 as a pitch, and a second deviation using the value smaller than the pitch $p_2$ of the second grating 3 as a pitch. The control unit 7 compares the acquired first deviation with the acquired second deviation. If the first deviation is smaller than the second deviation, the control unit 7 acquires a plurality of the sums Z of squares of deviation using a plurality of the pitches p larger than the pitch $p_2$ of the second grating 3. On the other hand, if the second deviation is smaller than the first deviation, the control unit 7 acquires a plurality of the sums Z of squares of deviation using a plurality of the pitches p smaller than the pitch $p_2$ of the second grating 3. The control unit 7 is configured to determine, as the pitch p of the intensity change 10*b*, the pitch p where the acquired plurality of sums Z of squares of deviation become smallest.

Figure 4:
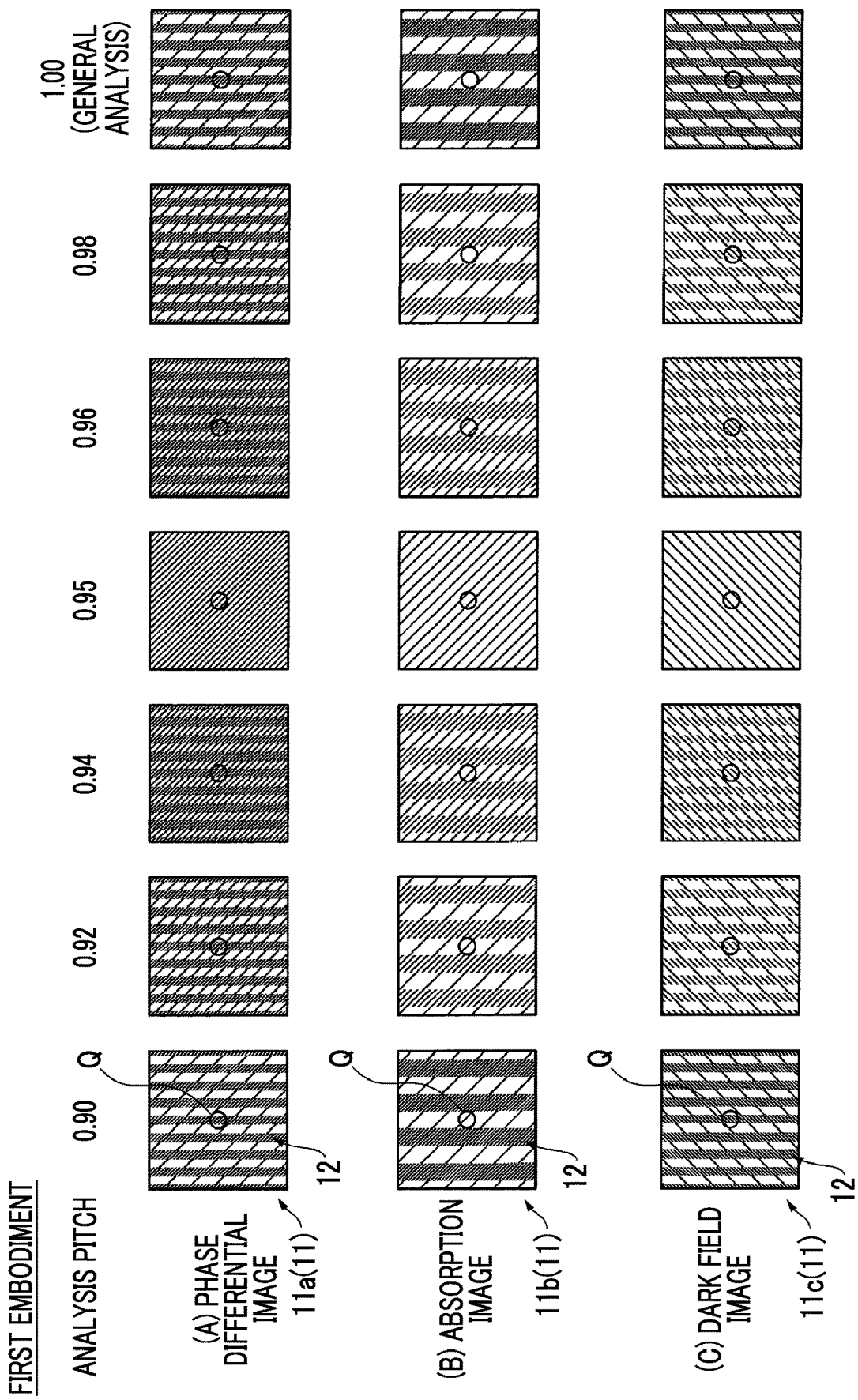
FIG. 4(A) is schematic view for describing a change in the artifact when the pitch is changed.
FIG. 4(B) is schematic view for describing a change in the artifact when the pitch is changed.
FIG. 4(C) is schematic view for describing a change in the artifact when the pitch is changed.

FIG. 4 shows an example where the phase differential image 11*a*, the absorption image 11*b*, and the dark field image 11*c* are generated by using the plurality of pitches, namely, the pitches p of the intensity change 30*b* which are smaller than the pitch $p_2$ of the second grating 3. An analysis pitch in FIG. 4 is a pitch obtained by multiplying the pitch $p_2$ of the second grating 3 by a predetermined coefficient. For example, an analysis pitch of 0.95 is a pitch (0.95×$p_2$)

obtained by multiplying the pitch $p_2$ of the second grating 3 by 0.95. It can be seen that as illustrated in FIG. 4, as the analysis pitch decreases from 1.00 to 0.95, the artifact 12 occurring in each image decreases. In addition, it can also be seen that if the analysis pitch further decreases from 0.95, the artifact 12 increases. Therefore, in the example shown in FIG. 4, a pitch where the sum Z of squares of deviation becomes smallest is an analysis pitch of 0.95 (0.95×$p_2$). Incidentally, the example shown in FIG. 4 is an example where a simulation is performed using 0.95×$p_2$ as the pitch p of the intensity change 30b. Therefore, actually, in order to determine the pitch p of the intensity change 30b, the control unit 7 is configured to set a plurality of the pitches p including the point of inflection at which the pitch p where the magnitude of the sum Z of squares of deviation decreases changes to the pitch p where the magnitude increases, and to determine, as the pitch p of the intensity change 30b, the pitch p where the sum Z of squares of deviation becomes the minimum value.

In the first embodiment, the image generation unit 6 calculates each pixel value of the phase contrast image 11 using the coefficients a, b, and c calculated from the equations (17) to (23) and the determined pitch p. The following equation (24) rewritten from the equation (9) is used when calculating each pixel value of the phase contrast image 11.

[Numeral 13]

$$y = A\sin\left(\frac{2\pi}{p}x + B\right) + C \quad (24)$$

Here, there is a relationship between coefficients A, B, and C and the coefficients a, b, and c which is expressed in the following equations (25) to (27). Incidentally, the unit in the following equation (26) is rad.

[Numeral 14]

$$A = \sqrt{a^2 + b^2} \quad (25)$$

$$B = \tan^{-1}\left(\frac{b}{a}\right) \quad (26)$$

$$C = c \quad (27)$$

If the coefficients A, B, and C of the equation (24) are used, the phase differential image 11a, the absorption image 11b, and the dark field image 11c can be expressed in the following equations (28) to (30).

[Numeral 15]

$$\varphi = \frac{p_2}{2\pi Z_T}(B_s - B_r) \quad (28)$$

$$T = \frac{C_s}{C_r} \quad (29)$$

$$D = \frac{A_s/C_s}{A_r/C_r} \quad (30)$$

Here, Φ is the phase differential image. In addition, T is the absorption image. In addition, D is the dark field image. In addition, subscripts s and r are a coefficient when an image is captured in a state where the object Q is present, and a coefficient when an image is captured in a state where the object Q is not present.

As described above, in the first embodiment, using the least square method, the control unit 7 is configured to fit the waveform shape of the intensity change 30b of the actually captured X-ray image and the waveform shape of the equation (9) to each other. Therefore, even though the pitch p of the intensity change 30b is shifted from the pitch $p_2$ of the second grating 3, it is possible to generate the phase contrast image 11 by obtaining the function (equation (9)) corresponding to the pitch p of the intensity change 30b.

(Method for Generating Phase Contrast Image)

Subsequently, a method for generating the phase contrast image 11 according to the first embodiment will be described with reference to FIG. 5.

In Step S1, the image generation unit 6 acquires an X-ray image which is a captured image of the object Q. Thereafter, the control unit 7 acquires data on the intensity change 30b in the pixel value of each pixel of the X-ray image which is a captured image of the object Q. Subsequently, in Step S2, the control unit 7 acquires a sum of squares of the first deviation by substituting a first pitch having a value, which is larger than the pitch $p_2$ of the second grating 3, into the function. In addition, the control unit 7 acquires a sum of squares of the second deviation by substituting a second pitch having a value, which is smaller than the pitch $p_2$ of the second grating 3, into the function. Incidentally, in Step S2, in order to acquire the sum of squares of the first deviation and the sum of squares of the second deviation, an equation including only the pitch p as a variable, which is obtained by solving the equation (9) using the equation (9), the equations (17) to (23), and a relational expression of m=2π/p, is used. Thereafter, the process proceeds to Step S3.

In Step S3, the control unit 7 compares the magnitude of the value of the sum of square of the first deviation with the magnitude of the value of the sum of squares of the second deviation. If the sum of squares of the first deviation is smaller than the sum of squares of the second deviation, the process proceeds to Step S4. If the sum of squares of the first deviation is larger than the sum of squares of the second deviation, the process proceeds to Step S5.

In Step S4, the control unit 7 sets a plurality of the pitches p, the values of which are smaller than the pitch $p_2$ of the second grating 3. In addition, in Step S5, the control unit 7 sets a plurality of the pitches p, the values of which are larger than the pitch $p_2$ of the second grating 3. Thereafter, the process proceeds to Step S6.

In Step S6, the control unit 7 acquires a plurality of the sums Z of squares of deviation using the plurality of pitches p which are set in Step S4 (Step S5). Thereafter, the control unit 7 acquires the pitch p where the plurality of sums Z of squares of deviation become smallest, and sets the pitch p as the pitch p of the function (equation (9)). Thereafter, in Step S7, the control unit 7 acquires the coefficients a to c of the function (equation (9)). Thereafter, in Step S8, the image generation unit 6 generates the phase contrast image 11 by using the function (equation (9)) where the pitch p acquired in Step S6 is determined, and the coefficients a to c acquired in Step S7, and ends the process.

(Effects of First Embodiment)

In the first embodiment, it is possible to obtain the following effects.

In the first embodiment, as described above, the phase contrast X-ray imaging system 100 includes the X-ray source 1; a plurality of gratings including the first grating 2 irradiated with an X-ray from the X-ray source 1 and the second grating 3 irradiated with the X-ray from the first grating 2; the detector 4 that detects the X-ray irradiated from the X-ray source 1; the grating movement mechanism 10 that moves the second grating 3; and the image processor 5 that generates the phase contrast image 11 based on the intensity change 30b indicating a change in the pixel value of each pixel detected by the detector 4. The image processor 5 is configured to generate the phase contrast image 11 by using the pitch p of the intensity change 30b and the function (equation (9)) which has the pitch as a variable and expresses the intensity change 30b in pixel value as the grating moves. Therefore, since the pitch p of the function (equation (9)) is a variable, it is possible to approximate the pitch p of the intensity change 30b, which is actually acquired while moving the second grating 3, by obtaining an optimal solution for the pitch p of the function (equation (9)). As a result, even though a shift occurs between the pitch p of the intensity change 30b in the pixel value of each pixel and the pitch $p_2$ of the second grating 3, since it is possible to adapt the pitch p of the function (equation (9)) to the pitch p of the intensity change 30b, it is possible to prevent the artifact 12 from occurring in the phase contrast image 11 to be obtained.

In addition, in the first embodiment, as described above, the pitch p of the intensity change 30b is a pitch including at least one shift of a shift in the pitch $p_2$ of the second grating 3 and a shift in the movement amount of the second grating 3 by the grating movement mechanism 10. Therefore, even though a shift occurs in either of the pitch $p_2$ of the second grating 3 and the movement amount of the second grating 3 (or, even though a shift occurs in both), it is possible to prevent the artifact 12 from occurring in the phase contrast image 11 to be generated by adapting the pitch p (variable) of the function (equation (9)) to the pitch p of the intensity change 30b which includes the shift.

In addition, in the first embodiment, as described above, the image processor 5 is configured to determine the pitch p of the intensity change 30b based on the data on the intensity change 30b acquired while moving the second grating 3, and the function (equation (9)). Therefore, it is possible to acquire the pitch p of the intensity change 30b from the actually measured data on the intensity change 30b. As a result, even though a shift occurs between the pitch p of the intensity change 30b and the pitch $p_2$ of the second grating 3, it is possible to acquire the pitch p of the intensity change 30b which includes the shift.

In addition, in the first embodiment, as described above, the image processor 5 is configured to determine the pitch p of the intensity change 30b by fitting the waveform shape of the intensity change 30b and the waveform shape of the function (equation (9)) to each other. Therefore, it is possible to determine the pitch p of the intensity change 30b based on the sum Z of squares of deviation between the waveform shape of the intensity change 30b and the waveform shape of the function (equation (9)). As a result, since it is possible to determine the pitch p of the intensity change 30b by comparing together the sums Z of squares of deviation acquired using a plurality of the pitches, for example, compared to the case where the pitch p of the intensity change 30b is determined by performing image processing on images acquired using a plurality of the pitches p, it is possible to further simplify the process of determining the pitch p of the intensity change 30b.

In addition, in the first embodiment, as described above, the sum Z of squares of deviation between the waveform shape of the intensity change 30b and the waveform shape of the function (equation (9)) is obtained using, as the pitch p, at least both of a value which is larger than the design value for the pitch $p_2$ of the second grating 3 moved by the grating movement mechanism 10 and a value which is smaller than the design value. Therefore, whether the pitch p where the sum Z of squares of deviation becomes smallest is a value larger than the design value for the pitch $p_2$ of the second grating 3 or a value smaller than the design value can be determined by comparing the first deviation calculated using the value larger than the design value for the pitch $p_2$ of the second grating 3 with the second deviation calculated using the value smaller than the design value for the pitch $p_2$ of the second grating 3. As a result, it is possible to easily determine the pitch p where the sum Z of squares of deviation becomes smallest.

In addition, in the first embodiment, as described above, the image processor 5 is configured to acquire the coefficients a to c of the function (equation (9)) which correspond to the predetermined pitch p, and to acquire the sum Z of squares of deviation between the waveform shape of the intensity change 30b and the waveform shape of the function (equation (9)) based on the coefficients a to c and the predetermined pitch p. Therefore, it is possible to acquire the sum Z of squares of deviation which corresponds to the predetermined pitch p. As a result, it is possible to easily determine the pitch p where the sum Z of squares of deviation becomes smallest by comparing together the sums Z of squares of deviation which correspond to a plurality of the pitches p.

Second Embodiment

Subsequently, a phase contrast X-ray imaging system 200 according to a second embodiment of the present invention will be described with reference to FIGS. 1 and 6. Unlike the first embodiment where the pitch p of the function is determined by comparing together a plurality of the sums Z of squares of deviation acquired using a plurality of the pitches p, in the second embodiment, the image processor 5 is configured to acquire the coefficients a to c of the function (equation (9)) from the pitch p of the intensity change 30b which is acquired in advance, and to generate the phase contrast image 11 based on the acquired coefficients a to c and the pitch p of the intensity change 30b which is acquired in advance. Incidentally, the same reference signs are assigned to the same configurations as those in the first embodiment, and the descriptions thereof are omitted.

Here, since the pitch $p_2$ of the second grating 3 is a very small value, the pitch $p_2$ may be slightly shifted due to manufacturing errors. In this case, even though a pitch (hereinafter, referred to as $p_x$) which is slightly shifted from the pitch $p_2$ of the second grating 3 is already known, in the general fringe scanning method using the equations (1) and (2), it is necessary to acquire data for the pitch k/N. However, if the accuracy of the grating movement mechanism 10 is not sufficient, since it is not possible to translationally move the second grating 3 by a movement amount ($p_x \times (k/N)$) obtained by dividing the already-known pitch $p_x$ by N, it is not possible to acquire the data for the pitch k/N, and the artifact 12 occurs. Then, in the second embodiment, the control unit 7 is configured to premeasure a shift in the pitch $p_2$ of the second grating 3. In addition, the control unit 7 is configured to determine the coefficients a to c by fitting an actual measurement value and the equation (9), into which the pitch $p_2$ of the intensity change 30b which is acquired in advance is substituted, to each other.

(Method for Generating Phase Contrast Image)

Subsequently, a method for generating the phase contrast image 11 according to the second embodiment will be described with reference to FIG. 6.

In Step S1, the control unit 7 acquires data on the intensity change 30b in the pixel value of each pixel of an X-ray image which is a captured image of the object Q. Subsequently, in Step S10, the control unit 7 acquires the pitch p of the intensity change 30b. Thereafter, in Step S11, the control unit 7 acquires the coefficients a to c of the equation (9) from the pitch p of the intensity change 30b which is acquired in advance. Thereafter, the process proceeds to Step S8.

In Step S8, the image generation unit 6 generates the phase contrast image 11 based on the acquired coefficients a to c and the pitch p of the intensity change 30b which is acquired in advance.

Incidentally, other configurations of the second embodiment are the same as those of the first embodiment.

(Effects of Second embodiment)

In the second embodiment, it is possible to obtain the following effects.

In the second embodiment, as described above, the image processor 5 is configured to acquire the coefficients a to c of the function (equation (9)) from the pitch p of the intensity change 30b which is acquired in advance, and to generate the phase contrast image 11 based on the acquired coefficients a to c and the pitch p of the intensity change 30b which is acquired in advance. Therefore, it is possible to acquire the coefficients a to c of the function (equation (9)) by fitting an actual measurement value and the function (equation (9)), into which the pitch p of the intensity change 30b which is acquired in advance is substituted, to each other. As a result, even though the movement amount of the second grating 3 is shifted, it is possible to determine the function (equation (9)) which accurately approximates actual data, and it is possible to prevent the artifact 12 from occurring in the phase contrast image 11 to be generated.

Incidentally, other effects of the second embodiment are the same as those of the first embodiment.

Modification Example

Incidentally, it should be considered that the embodiments disclosed this time are examples in all aspects and the present invention is not limited thereto. The scope of the present invention is not determined by the descriptions of the embodiments, but is as described in the claims, and further includes meanings equivalent to the claims and all changes (modification examples) within the scope.

For example, the first to third embodiments show an example where the first grating 2 and the second grating 3 are provided as a plurality of gratings; however, the present invention is not limited thereto. For example, as in a phase contrast X-ray imaging system 300 illustrated in FIG. 7, a third grating 40 may be provided between the X-ray source 1 and the first grating 2. The third grating 40 has a plurality of slits 40a and radioparent portions 40b which are arranged at a predetermined pitch $p_3$ in the direction X. Each of the slit 40a and the radioparent portion 40b extends straightly. In addition, the slit 40a and the radioparent portion 40b extend in parallel to each other. In addition, the third grating 40 is disposed between the X-ray source 1 and the first grating 2, and is irradiated with an X-ray from the X-ray source 1. The third grating 40 is configured such that an X-ray passing through each of the slits 40a serves as a line light source corresponding to the position of each of the slits 40a. Therefore, it is possible to enhance the coherence of the X-ray irradiated from the X-ray source 1 due to the third grating 40. As a result, since it is possible to form the self-image 20 of the first grating 2 without depending on a focal diameter of the X-ray source 1, it is possible to improve the degree of freedom in selecting the X-ray source 1.

In addition, the first and second embodiments show an example where a phase grating is used as the first grating 2; however, the present invention is not limited thereto. For example, an absorbent grating may be used as the first grating 2. If an absorbent grating is used as the first grating 2, the image processor 5 (image generation unit 6) generates the phase contrast image 11 by using a fringe pattern of an X-ray transmitting through the first grating 2, and the second grating 3. Therefore, since it is possible to acquire the phase contrast image 11 without using the self-image 20 of the first grating 2, it is possible to improve the degree of freedom in the position of disposition of the first grating 2. However, if an absorbent grating is used as the first grating 2, the image quality of the phase contrast image 11 to be obtained decreases, and thus if the phase contrast image 11 with a high image quality is desired to be obtained, a phase grating is preferably used as the first grating 2.

In addition, the first embodiment shows an example where values smaller than the pitch $p_2$ of the second grating 3 are used as a plurality of the pitches p which are used to acquire the sum Z of squares of deviation; however, the present invention is not limited thereto. For example, if the pitch p of the intensity change 30b is larger than the pitch $p_2$ of the second grating 3, values larger than the pitch $p_2$ of the second grating 3 may be used as the plurality of pitches p.

In addition, the first embodiment shows an example where the least square method is used to fit the waveform shape of the intensity change 30b and the waveform shape of the function to each other; however, the present invention is not limited thereto. Any fitting method may be used as long as it is possible to acquire the coefficients a to c of the function (equation (9)).

In addition, the first and second embodiments show an example where the grating movement mechanism 10 translationally moves the second grating 3; however, the present invention is not limited thereto. The first grating 2 may be translationally moved. A grating to be moved may be any grating.

In addition, the first and second embodiments show an example where the control unit 7 determines the sum Z of squares of deviation of the function (equation (9)); however, the present invention is not limited thereto. For example, a display unit may be provided to display, as illustrated in FIG. 4, a plurality of the phase contrast images 11 where the pitch p is changed, and the sum Z of squares of deviation of the function (equation (9)) may be determined by user's selection of the phase contrast images 11 displayed on the display unit.

The invention claimed is:
1. A phase contrast X-ray imaging system comprising:
an X-ray source;
a plurality of gratings including a first grating that is irradiated with an X-ray from the X-ray source, and a second grating that is irradiated with the X-ray from the first grating;
a detector that detects the X-ray irradiated from the X-ray source;
a grating movement mechanism that moves at least one of the plurality of gratings; and an image processor that generates a phase contrast image based on an intensity change indicating a change in a pixel value of each pixel detected by the detector, wherein the image processor generates the phase contrast image by using a pitch of the intensity change and a function which has the pitch as a variable which is an unknown number and expresses the intensity change in the pixel value as the grating moves.

2. The phase contrast X-ray imaging system according to claim 1, wherein the pitch of the intensity change is a pitch including at least one shift of a shift in a pitch of the grating and a shift in a movement amount of the grating by the grating movement mechanism.

3. The phase contrast X-ray imaging system according to claim 1, wherein the image processor determines the pitch of the intensity change based on data on the intensity change which is acquired by moving at least one of the plurality of gratings, and the function.

4. The phase contrast X-ray imaging system according to claim 1, wherein the image processor determines the pitch of the intensity change by fitting a waveform shape of the intensity change and a waveform shape of the function to each other.

5. The phase contrast X-ray imaging system according to claim 4, wherein the image processor obtains a deviation between the waveform shape of the intensity change and the waveform shape of the function using, as the pitch, at least both of a value which is larger than a design value for a pitch of the grating moved by the grating movement mechanism and a value which is smaller than the design value.

6. The phase contrast X-ray imaging system according to claim 4, wherein the image processor acquires a coefficient of the function which corresponds to a predetermined pitch, and acquires a deviation between the waveform shape of the intensity change and the waveform shape of the function based on the coefficient and the predetermined pitch.

7. The phase contrast X-ray imaging system according to claim 1, wherein the image processor acquires a coefficient of the function from a pitch of the intensity change which is acquired in advance, and generates the phase contrast image based on the acquired coefficient and the pitch of the intensity change which is acquired in advance.

8. The phase contrast X-ray imaging system according to claim 1, wherein the plurality of gratings further include a third grating that is disposed between the X-ray source and the first grating.

9. The phase contrast X-ray imaging system according to claim 1, wherein the deviation includes a first deviation and a second deviation, the first deviation is acquired by substituting a first pitch, which is larger than a pitch of the second grating, into the function, and the second deviation is acquired by substituting a second pitch, which is smaller than the pitch of the second grating, into the function.

10. The phase contrast X-ray imaging system according to claim 9, wherein a plurality of pitches of which values are decreasingly changed are set in response to a condition that the first deviation is larger than the second deviation, and a plurality of pitches of which values are increasingly changed are set in response to a condition that the first deviation is smaller than the second deviation.

11. The phase contrast X-ray imaging system according to claim 10, wherein a pitch of a smallest deviation among the plurality of pitches is acquired, and a coefficient of the function is acquired by using the pitch of the smallest deviation.

* * * * *